United States Patent [19]

Shields

[11] 4,076,659
[45] Feb. 28, 1978

[54] L-VAL[10]-SOMATOSTATIN AND INTERMEDIATES THERETO

[75] Inventor: James E. Shields, Indianapolis, Ind.

[73] Assignee: Eli Lilly and Company, Indianapolis, Ind.

[21] Appl. No.: 667,752

[22] Filed: Mar. 17, 1976

Related U.S. Application Data

[63] Continuation-in-part of Ser. No. 627,492, Oct. 30, 1975, abandoned.

[51] Int. Cl.² ............... C07C 103/52; C08L 37/00
[52] U.S. Cl. ............................ 260/8; 260/112.55
[58] Field of Search ........................... 260/112.55, 8

[56] References Cited

U.S. PATENT DOCUMENTS 3,933,784   1/1976   Sarantakis ................ 260/112.5 S

OTHER PUBLICATIONS

R. Walter, et al; Peptides: Chemistry, Structure and Biology, pp. 863-870 (1975).

Primary Examiner—Delbert R. Phillips
Assistant Examiner—B. Hazel
Attorney, Agent, or Firm—William C. Martens, Jr.; Everet F. Smith

[57] ABSTRACT

The tetradecapeptide

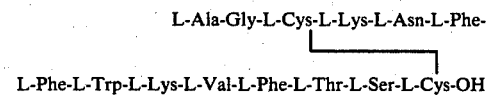

L-Phe-L-Trp-L-Lys-L-Val-L-Phe-L-Thr-L-Ser-L-Cys-OH is described along with corresponding non-toxic pharmaceutically-acceptable acid addition salts as well as intermediates useful in the synthesis of the tetradecapeptide. This tetradecapeptide as well as its pharmaceutically acceptable acid addition salts inhibit the release of growth hormone and the release of gastric acid.

9 Claims, No Drawings

L-VAL[10]-SOMATOSTATIN AND INTERMEDIATES THERETO

CROSS REFERENCE

This application is a continuation-in-part of application Ser. No. 627,492 filed Oct. 30, 1975, and now abandoned.

BACKGROUND AND SUMMARY OF THE INVENTION

This invention is directed to the tetradecapeptide

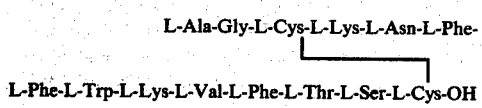

pharmaceutically acceptable acid addition salts and to intermediates produced during the synthesis of the tetradecapeptide.

Somatostatin (also known as somatotropin release inhibiting factor) is a tetradecapeptide of the formula

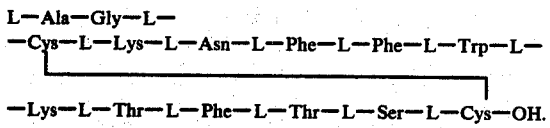

This tetradecapeptide was isolated from ovine hypothalamic extracts and was found to be active in inhibiting the secretion of growth hormone (GH), also known as somatotropin. In this regard, see P. Brazeau, W. Vale, R. Burgus, N. Ling, M. Butcher, J. Rivier, and R. Guillemin, Science, 179, 77 (1973).

The novel tetradecapeptide of this invention has the formula defined above and includes the non-toxic acid addition salts thereof. Its structure differs from that of somatostatin by the presence of a L-valine residue in position 10 in place of an L-threonine residue. For convenience sake, the tetradecapeptide of this invention can be referred to as L-Val[10]-somatostatin.

Thus, this invention is directed to a compound selected from those of the formula

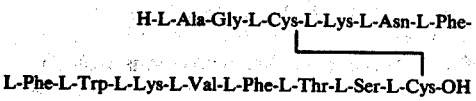

and pharmaceutically acceptable non-toxic acid addition salts, and R-L-Ala-Gly-L-Cys($R_1$)-L-Lys($R_2$)-L-Asn-L-Phe-L-Phe-L-Trp($R_5$)-L-Lys($R_2$)-L-Val-L-Phe-L-Thr($R_3$)-L-Ser($R_4$)-L-Cys($R_1$)-X; in which R is hydrogen or an α-amino protecting group;
$R_1$ is hydrogen or a thio protecting group;
$R_2$ is hydrogen or an ε-amino protecting group;
$R_3$ and $R_4$ each are hydrogen or a hydroxy protecting group;
$R_5$ is hydrogen or formyl; and
X is hydroxy or

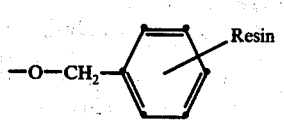

in which the resin is polystyrene; with the proviso that, when X is hydroxy, R, $R_1$, $R_2$, $R_3$, $R_4$, and $R_5$ each are hydrogen, and, when X is

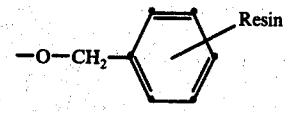

R, $R_1$, $R_2$, $R_3$, and $R_4$ each are other than hydrogen.

DETAILED DESCRIPTION OF THE INVENTION

As indicated above, this invention in part is directed to a compound conveniently referred to as L-Val[10]-somatostatin as well as to pharmaceutically acceptable non-toxic acid addition salts thereof.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salt is that prepared from acetic acid. Any of the above salts are prepared by conventional methods.

Also contemplated as being within the scope of this invention are intermediates of the formula R-L-Ala-Gly-L-Cys($R_1$)-L-Lys($R_2$)-L-Asn-L-Phe-L-Phe-L-Trp($R_5$)-L-Lys($R_2$)-L-Val-L-Phe-L-Thr($R_3$)-L-Ser($R_4$)-L-Cys($R_1$)-X.

Preferred intermediates include the following:

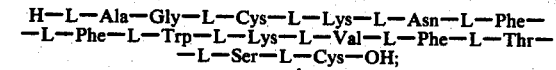
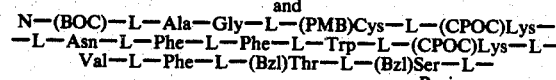
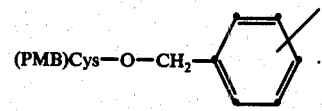

In the above formula defining the intermediates R is either hydrogen or an α-amino protecting group. The α-amino protecting groups contemplated for R are well recognized by those of ordinary skill in the peptide art. Many of these are detailed in the treatise *Protective Groups in Organic Chemistry*, J. F. W. McOmie, Editor, Plenum Press, New York, 1973, in Chapter 2, authored by J. W. Barton. Illustrative of such protecting groups are benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-methoxybenzyloxycarbonyl, p-nitrobenzyloxycarbonyl, t-butyloxycarbonyl (BOC), t-amyloxycarbonyl, 2-(p-biphenylyl)isopropyloxycarbonyl (BpOC), adamantyloxycarbonyl, isopropyloxycarbonyl, cyclopentyloxycarbonyl, cyclohexyloxycarbonyl, cycloheptyloxycarbonyl, triphenylmethyl (trityl), p-toluenesulfonyl, and the like. Preferably, the α-amino protecting group defined by R is t-butyloxycarbonyl.

$R_1$ represents either the hydrogen of the sulfhydryl group of the cysteine or a protecting group for the sulfhydryl substituent. Illustrative suitable such protecting groups are p-methoxybenzyl, benzyl, p-tolyl, benzhydryl, acetamidomethyl, trityl, p-nitrobenzyl, t-butyl, isobutyloxymethyl, as well as any of a number of trityl derivatives. For additional groups, see, for example, Houben-Weyl, *Methodes der Organischen Chemie,* "Synthese von Peptiden", Vols. 15/1 and 15/2, (1974), Stuttgart, Germany. Preferably, the sulfhydryl protecting group defined by $R_1$ is p-methoxybenzyl.

$R_2$ represents either hydrogen on the ε-amino function of the lysine residue or a suitable ε-amino protecting group. Illustrative such groups are the bulk of those mentioned hereinabove as being suitable for use as an α-amino protecting group. Included as typical such groups are benzyloxycarbonyl, t-butyloxycarbonyl, t-amyloxycarbonyl, cyclopentyloxycarbonyl, adamantyloxycarbonyl, p-methoxybenzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, isopropyloxycarbonyl, cyclohexyloxycarbonyl, cycloheptyloxycarbonyl, p-toluenesulfonyl, and the like.

As will become apparent hereinafter, the method of preparation of the tetradecapeptide of this invention involves periodic cleavage of the α-amino protecting group from the terminal amino acid present on the peptide chain. Thus, the only limitation with respect to the identity of the ε-amino protecting group on the lysine residue is that it be such that it will not be cleaved under the conditions employed in selectively cleaving the α-amino protecting group. Appropriate selection of the α-amino and the ε-amino protecting groups is a matter well within the knowledge of a peptide chemist of ordinary skill in the art and depends upon the relative ease with which a particular protecting group can be cleaved. Thus, groups such as 2-(p-biphenylyl)isopropyloxycarbonyl (BpOC) and trityl are very labile and can be cleaved even in the presence of mild acid. A moderately strong acid, such as hydrochloric acid, trifluoroacetic acid, or boron trifluoride in acetic acid, is required to cleave other groups such as t-butyloxycarbonyl, t-amyloxycarbonyl, adamantyloxycarbonyl, and p-methoxybenzyloxycarbonyl. Even stronger acid conditions are required to effect cleavage of other protecting groups such as benzyloxycarbonyl, halobenzyloxycarbonyl, p-nitrobenzyloxycarbonyl, cycloalkyloxycarbonyl, and isopropyloxycarbonyl. Cleavage of these latter groups requires drastic acid conditions such as the use of hydrogen bromide, hydrogen fluoride, or boron trifluoroacetate in trifluoroacetic acid. Of course, any of the more labile groups will also be cleaved under the stronger acid conditions. Appropriate selection of the amino protecting groups thus will include the use of a group at the α-amino function which is more labile than that employed as the ε-amino protecting group coupled with cleavage conditions designed to selectively remove only the α-amino function. In this context, $R_2$ preferably is cyclopentyloxycarbonyl, and, in conjunction therewith, the α-amino protecting group of choice for use in each of the amino acids which are added to the peptide chain preferably is t-butyloxycarbonyl.

The groups $R_3$ and $R_4$ both represent hydrogen or, separately, a protecting group for the alcoholic hydroxyl of threonine and serine, respectively. Typical such protecting groups are, for example, $C_1$-$C_4$ alkyl, such as methyl, ethyl, t-butyl, and the like; benzyl; substituted benzyl, such as p-methoxybenzyl, p-nitrobenzyl, o-chlorobenzyl, p-chlorobenzyl, and the like; $C_1$-$C_3$ alkanoyl, such as formyl, acetyl, and propionyl; triphenylmethyl (trityl); and the like. Preferably, when $R_3$ and $R_4$ are protecting groups, the protecting group of choice in both instances is benzyl.

The group $R_5$ represents either hydrogen or formyl, the latter being a protecting group for the NH of the tryptophan residue. The use of such a protecting group is optional and therefore $R_5$ properly can be hydrogen (N-unprotected) or formyl (N-protected).

The group X represents the carboxyl terminal of the tetradecapeptide chain and can be hydroxyl in which case a free carboxyl group thereby is defined. In addition, X represents the solid resin support to which the carboxyl terminal moiety of the peptide is linked during its synthesis. This solid resin can be represented by the formula

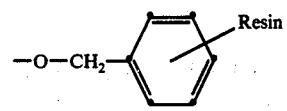

In any of the above, when X represents hydroxyl, R, $R_1$, $R_2$, $R_3$, $R_4$, and $R_5$ each are hydrogen. When X represents the solid resin support, R, $R_1$, $R_2$, $R_3$, and $R_4$ each represent a protecting group.

The following abbreviations, most of which are well known and commonly used in the art, are employed herein:

Ala — Alanine
Asn — Asparagine
Cys — Cysteine
Gly — Glycine
Lys — Lysine
Phe — Phenylalanine
Ser — Serine
Thr — Threonine
Trp — Tryptophan
Val — Valine
DCC — N,N′-Dicyclohexylcarbodiimide
DMF — N,N-Dimethylformamide
BOC — t-Butyloxycarbonyl
PMB — p-Methoxybenzyl
CPOC — Cyclopentyloxycarbonyl
Bzl — Benzyl
BpOC — 2-(p-biphenylyl)isopropyloxycarbonyl Although the selection of the particular protecting groups to be employed in preparing the compounds of this invention remains a matter well within the ordinary skill of a synthetic peptide chemist, it is well to recognize that the proper selection of the protecting groups is dependent upon the particular succeeding reactions which must be carried out. Thus, the protecting group of choice must be one which is stable both to the reagents and under the conditions employed in the succeeding steps of the reaction sequence. For example, as already discussed to some degree hereinabove, the particular protecting group which is employed must be one which remains intact under the conditions which are employed for cleaving the α-amino protecting group of the terminal amino acid residue of the peptide fragment in preparation for the coupling of the next succeeding amino acid fragment to the peptide chain. It is also important to select, as protecting group, one which will remain intact during the building of the peptide chain and which will be readily removable upon completion of the synthesis of the desired tetradecapeptide product. All of these matters are well within the knowledge and understanding of a peptide chemist of ordinary skill in the art.

As is evident from the above discussion, the tetradecapeptide of this invention can be prepared by solid phase synthesis. This synthesis involves a sequential building of the peptide chain beginning at the C-terminal end of the peptide. Specifically, cysteine first is linked at its C-terminal to the resin by reaction of an amino-protected, S-protected cysteine with a chloromethylated resin or a hydroxymethyl resin. Preparation of a hydroxymethyl resin is described by Bodanszky et al., Chem. Ind. (London), 38 1597–98 (1966). The chloromethylated resin is commercially available from Lab Systems, Inc., San Mateo, Calif.

In accomplishing linkage of the C-terminal cysteine to the resin, the protected cysteine first is converted to its cesium salt. This salt then is reacted with the resin in accordance with the method described by B. F. Gisin, Helv. Chim. Acta, 56, 1476 (1973). Alternatively, the cysteine can be linked to the resin by activation of the carboxyl function of the cysteine molecule by application of readily recognized techniques. For example, the cysteine can be reacted with the resin in the presence of a carboxyl group activating compound such as N,N'-dicyclohexylcarbodiimide (DCC).

Once the C-terminal cysteine has been appropriately linked to the resin support, the remainder of the peptide building sequence involves the step-wise addition of each amino acid to the N-terminal portion of the peptide chain. Necessarily, therefore, the particular sequence which is involved comprises a cleavage of the α-amino protecting group from the amino acid which represents the N-terminal portion of the peptide fragment followed by coupling of the next succeeding amino acid residue to the now free and reactive N-terminal amino acid. Cleavage of the α-amino protecting group can be effected in the presence of an acid such as hydrobromic acid, hydrochloric acid, trifluoroacetic acid, p-toluenesulfonic acid, benzenesulfonic acid, naphthalenesulfonic acid, acetic acid, and the like, with formation of the respective acid addition salt product. Another method which is available for accomplishing cleavage of the amino protecting group involves the use of boron trifluoride. For example, boron trifluoride diethyl etherate in glacial acetic acid will convert the amino-protected peptide fragment to a $BF_3$ complex which then can be converted to the deblocked peptide fragment by treatment with a base such as aqueous potassium bicarbonate. Any of these methods can be employed as long as it is recognized that the method of choice must be one which accomplishes cleavage of the N-terminal α-amino protecting group without disruption of any other protecting groups present on the peptide chain. In this regard, it is preferred that the cleavage of the N-terminal protecting group be accomplished using trifluoroacetic acid. Generally, the cleavage will be carried out at a temperature from about 0° C. to about room temperature.

Once the N-terminal cleavage has been effected, the product which results normally will be in the form of the acid addition salt of the acid which has been employed to accomplish the cleavage of the protecting group. The product then can be converted to the free terminal amino compound by treatment with a mild base, typically a tertiary amine such as pyridine, triethylamine, or the like.

The peptide chain then is ready for reaction with the next succeeding amino acid. This can be accomplished by employing any of several recognized techniques. In order to achieve coupling of the next-succeeding amino acid to the N-terminal peptide chain, an amino acid which has a free carboxyl but which is suitably protected at the α-amino function as well as at any other active moiety is employed. The amino acid then is subjected to conditions which will render the carboxyl function active to the coupling reaction. One such activation technique which can be employed in the synthesis involves the conversion of the amino acid to a mixed anhydride. Thereby, the free carboxyl function of the amino acid is activated by reaction with another acid, typically a carbonic acid in the form of its acid chloride. Examples of such acid chlorides which can be used to form the appropriate mixed anhydrides are ethyl chloroformate, phenyl chloroformate, sec-butyl chloroformate, isobutyl chloroformate, pivaloyl chloride, and the like.

Another method of activating the carboxyl function of the amino acid to achieve coupling is by conversion of the amino acid to its active ester derivative. Examples of such active esters are, for example, a 2,4,5-trichlorophenyl ester, a pentachlorophenyl ester, a p-nitrophenyl ester, an ester formed from 1-hydroxybenzotriazole, and an ester formed from N-hydroxysuccinimide. Another method for effecting coupling of the C-terminal amino acid to the peptide fragment involves carrying out the coupling reaction in the presence of at least an equimolar quantity of N,N'-dicyclohexylcarbodiimide (DCC). This latter method is preferred for preparing the tetradecapeptide of this invention.

Once the desired amino acid sequence has been prepared, the resulting peptide can be removed from the resin support. This is accomplished by treatment of the protected resin-supported tetradecapeptide with hydrogen fluoride. Treatment with hydrogen fluoride cleaves the peptide from the resin; in addition, however, it cleaves all remaining protecting groups present on the reactive moieties located on the peptide chain as well as the α-amino protecting group present at N-terminal amino acid. When hydrogen fluoride is employed to effect the cleavage of the peptide from the resin as well as removal of the protecting groups, it is preferred that the reaction be carried out in the presence of anisole. The presence of anisole has been found to inhibit the potential alkylation of certain amino acid residues present in the peptide chain. In addition, it is preferred that the cleavage be carried out in the presence of ethyl mercaptan. The ethyl mercaptan serves to protect the indole ring of the tryptophan residue and, furthermore, facilitates conversion of the blocked cysteines to their thiol forms. Also, when $R_5$ is formyl, the presence of ethyl mercaptan facilitates hydrogen fluoride cleavage of the formyl group.

Once the cleavage reaction has been accomplished, the product which is obtained is a straight-chain peptide containing 14 amino acid residues. In order to obtain the final product of this invention, it is necessary to treat the straight-chain tetradecapeptide under conditions which will effect its oxidation by converting the two sulfhydryl groups present in the molecule, one at each cysteinyl moiety, to a disulfide bridge. This can be accomplished by treating a dilute solution of the linear tetradecapeptide with any of a variety of oxidizing agents including, for example, iodine, potassium ferricyanide, and the like. Air also can be employed as oxidizing agent, the pH of the mixture generally being from about 2.5 to about 9.0, and preferably from about 7.0 to about 7.6. The concentration of the solution which is employed generally is not greater than about 0.4 mg. of the peptide per milliliter of solution, and usually is about 50 µg./ml.

The compounds of this invention having the disulfide linkage may be administered to warm-blooded mammals, including humans, by any of several methods, including orally, sublingually, subcutaneously, intramuscularly, intravenously, and the like. Administration of these compounds will inhibit the release of growth hormone. This inhibitory effect is beneficial in those instances in which the host being treated requires a therapeutic treatment for excess secretion of somatotropin, such secretion being associated with adverse conditions such as juvenile diabetes and acromegaly. In addition, administration of these compounds will inhibit the secretion of gastric acid. This inhibitory effect is beneficial in those instances in which the host being treated requires therapeutic treatment, for example, of an ulcer condition. Preferably, the dose range for sublingual or oral administration is about 1 mg. to about 100 mg./kg. of body weight per day. Generally, the dose range for intravenous, subcutaneous, or intramuscular administration is from about 10 µg. to about 1 mg./kg. of body weight per day, and, preferably, is from about 50 µg. to about 100 µg./kg. of body weight per day. It is evident that the dose range will vary widely dependent upon the particular condition which is being treated as well as the severity of the condition.

It is also possible to administer the compounds of this invention in the form of tablets containing other inocuous ingredients. Inert diluents or carriers, for example, magnesium carbonate or lactose, can be used together with conventional disintegrating agents, for example, maize starch and alginic acid, and lubricating agents, for example, magnesium stearate. Typically, the amount of carrier or diluent will range from about 5 to about 95 percent of the final composition, and preferably from about 50 to about 85 percent of the final composition. Suitable flavoring agents also can be employed in the final preparation rendering the composition more palatable for administration.

When the compounds of this invention are to be administered intravenously, suitable carriers may be employed, such as, for example, isotonic saline, phosphate buffer solutions, and the like.

The following examples are illustrative of the preparation of compounds of this invention.

EXAMPLE 1

N-t-BUTYLOXYCARBONYL-L-CYSTEINYL(S-p-METHOXYBENZYL) METHYLATED POLYSTYRENE RESIN

To 20.0 g. of chloromethylated polystyrene resin (Lab Systems, Inc., 0.75 mmoles/gram) suspended in 150 ml. of N,N-dimethylformamide (DMF) were added 3.7 grams (7.8 mmoles) of the cesium salt of N-t-butyloxycarbonyl-(S-p-methoxybenzyl)cysteine. The mixture was stirred at room temperature for three days. The resin then was filtered and washed successively with DMF, a mixture of 90 percent DMF and 10 percent water, and DMF. To the resin suspended in DMF was added a solution of 5.5 grams of cesium acetate in hot DMF. The mixture was stirred overnight at room temperature, for 8 hours at 50° C., overnight at room temperature, for 8 hours at 50° C., and for three days at room temperature. The resin then was filtered and was washed successively with DMF, a mixture of 90 percent DMF and 10 percent water, DMF, a mixture of 90 percent DMF and 10 percent water, DMF, and 95 percent ethanol. The resin then was dried in vacuo at 50° C. to obtain the title product containing 0.45 percent nitrogen (0.32 mmole/gram) and 0.80 percent sulfur (0.25 mmole/gram).

EXAMPLE 2 t-BUTYLOXYCARBONYL-L-ALANYL-GLYCYL-L-(S-p-METHOXYBENZYL)CYSTEINYL-L-(CYCLOPENTYLOXYCARBONYL)-LYSYL-L-ASPARAGINYL-L-PHENYLALANYL-L-PHENYLALANYL-L-TRYPTOPHYL-L-(N-CYCLOPENTYLOXYCARBONYL)LYSYL-L-VALYL-L-PHENYLALANYL-L-(O-BENZYL)-THREONYL-L-(O-BENZYL)SERYL-L-(S-p-METHOXY-BENZYL)CYSTEINYL METHYLATED POLYSTYRENE RESIN

To a 300 ml. reaction vessel on a rocker were added 16.26 grams of the product from Example 1. Sequences of deprotection, neutralization, coupling, and a recoupling were carried out for the addition of each amino acid to the peptide. Addition of the first three amino acids to the cysteine-resin was carried out manually. The resulting tetrapeptide resin (2.0 grams) then was placed in the reaction vessel of a Beckman 990 automatic peptide synthesizer, and the remaining ten amino acids were added employing the automatic synthesizer. The amino acids which were employed as well as the sequence of their employment is as follows: (1) N-t-butyloxycarbonyl-(O-benzyl)-L-serine; (2) N-t-butyloxycarbonyl-(O-benzyl)-L-threonine; (3) N-t-butyloxycarbonyl-L-phenylalanine; (4) N-t-butyloxycarbonyl-L-valine; (5) $N^\alpha$-t-butyloxycarbonyl-$N^\epsilon$-cyclopentyloxycarbonyl-L-lysine; (6) $N^\alpha$-t-butyloxycarbonyl-N-formyl-L-tryptophan; (7) N-t-butyloxycarbonyl-L-phenylalanine; (8) N-t-butyloxycarbonyl-L-phenylalanine; (9) N-t-butyloxycarbonyl-L-asparagine p-nitrophenyl ester; (10) $N^\alpha$-t-butyloxycarbonyl-$N^\epsilon$-cyclopentyloxycarbonyl-L-lysine; (11) N-t-butyloxycarbonyl-(S-p-methoxybenzyl)-L-cysteine; (12) N-t-butyloxycarbonylglycine; and (13) N-t-butyloxycarbonyl-L-alanine. The sequence of deprotection, neutralization, coupling, and recoupling for the introduction of each amino acid into the peptide is as follows: (1) three washes (7.5–15 ml./gram resin) of 3 minutes each with methylene chloride; (2) removal of BOC group by treatment twice for ten minutes each with 7.5–15 ml./gram resin of a mixture of 48 percent trifluoroacetic acid, 47 percent methylene chloride, and 5 percent triethylsilane; (3) three washes (7.5–15 ml./gram resin) of 3 minutes each with methylene chloride; (4) three washes (7.5–15 ml./gram resin) of three minutes each with a mixture of 95 percent t-butyl alcohol and 5 percent methylene chloride; (5) three washes (7.5–15 ml./gram resin) of 3 minutes each with methylene chloride; (6) neutralization by three treatments of 3 minutes each with 7.5–15 ml./gram resin of 3 percent triethylamine in methylene chloride; (7) three washes (7.5–15 ml./gram resin) of 3 minutes each with methylene chloride; (8) three washes (7.5–15 ml./gram resin) of 3 minutes each with a mixture of 95 percent t-butyl alcohol and 5 percent methylene chloride; (9) three washes (7.5–15 ml./gram resin) of 3 minutes each with methylene chloride; (10) addition of 1.0 mmole/gram resin of the protected amino acid and 1.0 mmole/gram resin of N,N'-dicyclohexylcarbodiimide (DCC) in 7.5-15 ml./gram resin of methylene chloride followed by mixing for 120 minutes; (11) three washes (7.5-15 ml./gram resin) of 3 minutes each with methylene chloride; (12) three washes (7.5-15 ml./gram resin) of 3 minutes each with a mixture of 95 percent t-butyl alcohol and 5 percent methylene chloride; (13) three washes (7.5-15 ml./gram resin) of 3 minutes each with methylene chloride; (14) neutralization by three treatments of 3 minutes each with 7.5-15 ml./gram resin of 3 percent triethylamine in methylene chloride; (15) three washes (7.5-15 ml./gram resin) of 3 minutes each with methylene chloride; (16) three washes (7.5-15 ml./gram resin) of 3 minutes each with a mixture of 95 percent t-butyl alcohol and 5 percent methylene chloride; (17) three washes (7.5-15 ml./gram resin) of 3 minutes each with methylene chloride; (18) three washes (7.5-15 ml./gram resin) of 3 minutes each with DMF; (19) addition of 1.0 mmole/gram resin of the protected amino acid and 1.0 mmole/gram resin of N,N'-di-cyclohexylcarbodiimide (DCC) in 7.5-15 ml./gram resin of a 1:1 mixture of DMF and methylene chloride followed by mixing for 120 minutes; (20) three washes (7.5-15 ml./gram resin) of 3 minutes each with DMF; (21) three washes (7.5-15 ml./gram resin) of 3 minutes each with methylene chloride; (22) three washes (7.5-15 ml./gram resin) of 3 minutes each with a mixture of 95 percent t-butyl alcohol and 5 percent methylene chloride; (23) three washes (7.5-15 ml./gram resin) of 3 minutes each with methylene chloride; (24) neutralization by three treatments of 3 minutes each with 7.5-15 ml./gram resin of 3 percent triethylamine in methylene chloride; (25) three washes (7.5-15 ml./gram resin) of 3 minutes each with methylene chloride; (26) three washes (7.5-15 ml./gram resin) of 3 minutes each with a mixture of 95 percent t-butyl alcohol and 5 percent methylene chloride; and (27) three washes (7.5-15 ml./gram resin) of 3 minutes each with methylene chloride. With the exception of the asparagine residue, each amino acid was incorporated by means of the above sequence. The asparagine residue was incorporated via its p-nitrophenyl active ester. In doing so, Step (10) above was modified to the following 3-step sequence: (a) three washes (7.5-15 ml./gram resin) of 3 minutes each with DMF; (b) addition of 1.0 mmole/gram resin of the p-nitrophenyl ester of N-t-butyloxycarbonyl-L-asparagine in 7.5-15 ml./gram resin of a 1:1 mixture of DMF and methylene chloride followed by mixing for 720 minutes; and (c) three washes (7.5-15 ml./gram resin) of 3 minutes each with DMF. Also, Step (19) was altered to duplicate the above Step (b) with the exception that a 3:1 mixture of DMF and methylene chloride was employed.

The finished peptide-resin was dried in vacuo. A portion of the product was hydrolyzed by refluxing for 21 hours in a mixture of hydrochloric acid and dioxane. Amino acid analysis of the resulting product gave the following results, lysine being employed as standard: Asn, 0.94; Thr, 1.17; Ser, 0.91; Gly, 0.91; Ala, 0.96; Val, 1.11; Phe, 3.03; Lys, 2.00. The presence of tryptophan and cysteine was not determined since both are destroyed by the method of analysis.

EXAMPLE 3

L-ALANYL-GLYCYL-L-CYSTEINYL-L-LYSYL-L-ASPARAGINYL-L-PHENYLALANYL-L-PHE-NYL-ALANYL-L-TRYPTOPHYL-L-LYSYL-L-VALYL-L-PHENYLALANYL-L-THREONYL-L-SERYL-L-CYSTEINE

To a mixture of 10 ml. of anisole and 10 ml. of ethyl mercaptan were added 2.55 grams of the protected tetradecapeptide-resin of Example 2. The mixture was cooled in liquid nitrogen, and 43 ml. of liquid hydrogen fluoride were added by distillation. The resulting mixture was allowed to warm to 0° C. and was stirred for 1.5 hours. The hydrogen fluoride then was distilled off, and ether was added to the remaining mixture. The resulting solid material was collected by filtration and washed with ether. The product was dried, and the deprotected tetradecapeptide was extracted from the resin mixture using 1M acetic acid. The acetic acid solution then was immediately lyophilized to dryness in the dark. The resulting white solid was suspended in a mixture of 15 ml. of 1M acetic acid and 5 ml. of glacial acetic acid. The resulting suspension was filtered, and the filtrate was absorbed on a Sephadex G-25 F column. The chromatographic conditions were: solvent, deoxygenated 1M acetic acid; column size, 7.5 × 155 cm.; temperature, 26° C.; flow rate, 640 ml./hour; fraction volume, 22.4 ml.

Absorbance at 280 m$\mu$ of each fraction plotted versus fraction number indicated two main peaks with shoulders. A collection of four sets of fractions was made. The fractions which were combined and their effluent volumes are as follows:

Fractions 191-204 (4257-4570 ml.)
Fractions 205-219 (4571-4906 ml.)
Fractions 220-234 (4907-5242 ml.)
Fractions 235-294 (5243-6586 ml.)

The four samples were lyophilized to dryness in the dark and collected. The amounts of product which were collected for each of the four samples were 17.8 mg., 32.7 mg., 44.9 mg., and 95.4 mg., respectively. UV spectroscopy and amino acid analysis indicated that the second sample was the best product. The amino acid analysis of this sample is as follows: $Ala_{0.93}$ $Gly_{0.95}$ $Cys_{0.81}$ $Lys_{1.0}$ $Asn_{0.96}$ $Phe_{0.92}$ $Phe_{0.92}$ $Trp_{0.69}$ $Lys_{1.0}$ $Val_{0.93}$ $Phe_{0.92}$ $Thr_{0.97}$ $Ser_{0.82}$ $Cys_{0.81}$.

EXAMPLE 4

OXIDATION TO L-$Val^{10}$-SOMATOSTATIN

The reduced L-$Val^{10}$-somatostatin from Example 3 (3.75 mg.) was dissolved in 15 ml. of 0.2 M acetic acid. A UV spectrum of the resulting solution indicated a concentration of 160 $\mu$g./ml. The solution was diluted with 33 ml. of distilled water to achieve a 50 $\mu$g./ml. concentration. Concentrated ammonium hydroxide was added to adjust the pH of the mixture to 8.0. The solution was stirred at room temperature in the dark for 23 hours after which an Ellman titration indicated that oxidation was complete. The mixture was acidified with 1 ml. of glacial acetic acid and lyophilized to dryness. A second lyophilization from distilled water was made.

The resulting white solid was dissolved in 2 ml. of deoxygenated 0.2 M acetic acid. The solution was absorbed on a Sephadex G-25 F column. The chromatographic conditions were as follows: solvent, deoxygenated 0.2 M acetic acid; column size, 0.9 × 160 cm.;

temperature, 26° C.; flow rate, 15.2 ml./hour; fraction volume, 3.3 ml.

Absorbance at 280 mµ for each fraction plotted versus fraction number indicated one large peak with two smaller peaks preceding it. UV spectroscopy showed the large peak to be good product. This peak accounted for 68 percent of the material on the graph. Fractions 26–34 were combined (effluent volumes of 87.9–111 ml.) and lyophilized to dryness to obtain the desired product.

Optical rotation $[\alpha]_D^{26} = -48.7°$ (1 percent acetic acid).

Amino acid analysis: $Ala_{0.92}$ $Gly_{1.06}$ $Cys_{0.95}$ $Lys_{1.0}$ $Asn_{1.10}$ $Phe_{0.91}$ $Phe_{0.91}$ $Trp_{0.83}$ $Lys_{1.0}$ $Val_{1.0}$ $Phe_{0.91}$ $Thr_{1.08}$ $Ser_{0.95}$ $Cys_{0.95}$.

The product from Example 4 was tested for its activity in inhibiting the release of growth hormone. The procedure which was employed is carried out using mature male Spraque-Dawley rats (Laboratory Supply Company, Indianapolis, Indiana). The test is a modification of the method of P. Brazeau, W. Vale, and R. Guilleman, *Endocrinology,* 94 184 (1974). In this assay, five groups of eight rats each were employed. First, sodium pentobarbitol was administered to all 40 rats to stimulate growth hormone secretion. One of the groups of eight rats is the control group and received only saline. Two of the groups received somatostatin, one at 2 µg./rat, subcutaneously, and the other at 50 µg./rat, subcutaneously. The other two groups received L-Val[10]-somatostatin, one at 2 µg./rat, subcutaneously and the other at 50 µg./rat, subcutaneously. The degree of inhibition of serum growth hormone concentration then was determined with respect to the control group, and the relative activities of L-Val[10]-somatostatin and somatostatin itself were compared.

At a dose level of 2 µg./rat, L-Val[10]-somatostatin diminished the serum growth hormone concentration by 49 percent over control whereas somatostatin had no effect whatever on the serum growth hormone concentration. At a dose level of 50 µg./rat, L-Val[10]-somatostatin diminished the serum growth hormone concentration by 72 percent over control, while somatostatin itself produced a 91 percent inhibition.

I claim:

1. A compound of the formula

H-L-Ala-Gly-L-Cys-L-Lys-L-Asn-L-Phe-
L-Phe-L-Trp-L-Lys-L-Val-L-Phe-L-Thr-L-Ser-L-Cys-OH and its pharmaceutically acceptable non-toxic addition salts, and intermediates to said compound, said intermediates having the formula R-L-Ala-Gly-L-Cys($R_1$)-L-Lys($R_2$)-L-Asn-L-Phe-L-Phe-L-Trp($R_5$)-L-Lys($R_2$)-L-Val-L-Phe-L-Thr($R_3$)-L-Ser($R_4$)-L-Cys($R_1$)-X; in which:

R is hydrogen or an α-amino protecting group;
$R_1$ is hydrogen or a thio protecting group;
$R_2$ is hydrogen or an ε-amino protecting group;
$R_3$ and $R_4$ each are hydrogen or a hydroxy protecting group;
$R_5$ is hydrogen or formyl; and
X is hydroxy or

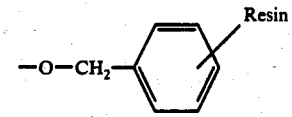

in which the resin is polystyrene; with the proviso that, when X is hydroxy, R, $R_1$, $R_2$, $R_3$, $R_4$, and $R_5$ each are hydrogen, and, when X is

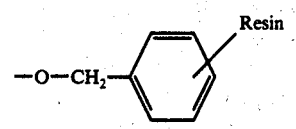

R, $R_1$, $R_2$, $R_3$, and $R_4$ each are other than hydrogen.

2. Compound of claim 1, having the formula

H-L-Ala-Gly-L-Cys-L-Lys-L-Asn-L-Phe-
L-Phe-L-Trp-L-Lys-L-Val-L-Phe-L-Thr-L-Ser-L-Cys-OH and pharmaceutically acceptable non-toxic acid addition salts thereof.

3. Compound of claim 1, having the formula R-L-Ala-Gly-L-Cys($R_1$)-L-Lys($R_2$)-L-Asn-L-Phe-L-Phe-L-Trp($R_5$)-L-Lys($R_2$)-L-Val-L-Phe-L-Thr($R_3$)-L-Ser($R_4$)-L-Cys($R_1$)-X.

4. Compound of claim 3, in which X is hydroxy.

5. Compound of claim 3, in which R is t-butyloxycarbonyl.

6. Compound of claim 3, in which $R_1$ is p-methoxybenzyl.

7. Compound of claim 3, in which $R_2$ is cyclopentyloxycarbonyl.

8. Compound of claim 3, in which $R_3$ and $R_4$ are benzyl.

9. Compound of claim 3, having the formula

N—(BOC)—L—Ala—Gly—L—(PMB)Cys—L—
—(CPOC)Lys—L—Asn—L—Phe—L—Phe—L—Trp—L—
—(CPOC)Lys—L—Val—L—Phe—L—(Bzl)Thr—L—(Bzl)—
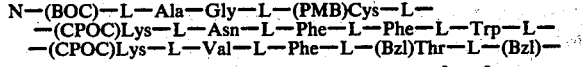
Ser—L—(PMB)Cys—O—CH$_2$—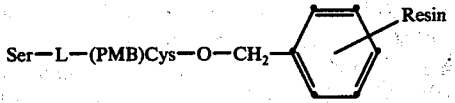

* * * * *